United States Patent
Cosimbescu et al.

(10) Patent No.: US 7,026,481 B2
(45) Date of Patent: Apr. 11, 2006

(54) SYNTHESIS FOR QUINACRIDONE COMPOUNDS

(75) Inventors: Lelia Cosimbescu, Rochester, NY (US); Jianmin Shi, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 226 days.

(21) Appl. No.: 10/184,281

(22) Filed: Jun. 27, 2002

(65) Prior Publication Data

US 2004/0002605 A1 Jan. 1, 2004

(51) Int. Cl.
*C07D 471/02* (2006.01)

(52) U.S. Cl. .......................................... 546/49; 546/56
(58) Field of Classification Search .................. 546/49, 546/56

See application file for complete search history.

(56) References Cited

U.S. PATENT DOCUMENTS 4,544,746 A * 10/1985 Holtje .......................... 546/49
6,241,814 B1 * 6/2001 Urban et al. ................. 106/497
6,376,107 B1   4/2002 Heuer et al. ................. 428/690

OTHER PUBLICATIONS

Morrison & Boyd, Oragnic Chemistry, 3$^{rd}$ ed. 1974, pp 735, 823 827.*

Shi et al, Macromolecules vol. 34 No. 19 pp 6571–6576 (2001) "Conjugated Polymers Contaqinong Arylamine Pendants for Light–Emitting Diodes".*

* cited by examiner

*Primary Examiner*—Rita Desai
*Assistant Examiner*—Raymond Covington
(74) *Attorney, Agent, or Firm*—Arthur E. Kluegel

(57) ABSTRACT

Disclosed is a process for forming a N,N'-diarylquinacridone compound comprising the step of reacting a 1,4-dialkylcarboxylate-2,5-bis(N-arylamino) benzene with an iodoaryl compound to form the corresponding 2,5-bis(N-diarylamino) compound. The process is versatile and provides high yields and purity for the synthesis of N,N'-diarylquinacridone compounds.

17 Claims, No Drawings

SYNTHESIS FOR QUINACRIDONE COMPOUNDS

FIELD OF THE INVENTION

This invention relates to the field of organic syntheses and to a process for forming a N,N'-diarylquinacridone compound comprising the step of reacting a 1,4-dialkylcarboxylate-2,5-bis(N-arylamino) benzene with an iodoaryl compound to form the corresponding 2,5-bis(N-diarylamino) compound.

BACKGROUND OF THE INVENTION

N,N'-diarylquinacridones have become useful materials and have necessitated synthetic methods for preparing them. In U.S. Pat. No. 6,376,107, Heuer et al disclose the preparation of N,N'-dialkylquinacridones by contacting unsubstituted quinacridones and alkyl halides with a base such as sodium hydride, in a solvent such as dimethylacetamide or dimethylformamide. This is however not extended to the case of aryl halides.

Radl et al, in a series of disclosures (Czech patents 262587, and 261338), disclose the reaction of 4-oxodihydroquinolines with nitroaryl halides with a base such as sodium hydride in a solvent such as dimethylformamide. The disclosure only teaches the use of aryl halides including nitro groups, and those skilled in the art will realize that aryl halides with other substituents, or no substituents at all, will not react as efficiently in this way.

It is a problem to be solved to provide a process for the synthesis of N,N'-diarylquinacridone compounds that is versatile and provides high yields and purity.

SUMMARY OF THE INVENTION

The invention provides a process for forming a N,N'-diarylquinacridone compound comprising the step of reacting a 1,4-dialkylcarboxylate-2,5-bis(N-arylamino) benzene with an iodoaryl compound to form the corresponding 2,5-bis(N-diarylamino) compound. The process is versatile and provides high yields and purity for the synthesis of N,N'-diarylquinacridone compounds.

DETAILED DESCRIPTION OF THE INVENTION

The invention process is summarized above. The process is useful for synthesizing an intermediate in the preparation of N,N'-diaryl quinacridones comprising the step of contacting a 1,4-dialkylcarboxylate-2,5-bis(N-arylamino) benzene with an iodoaryl compound to form a 1,4-dialkylcarboxylate-2,5-bis(N,N'-diarylamino) benzene in the presence of a base, a metal, an optional solvent, and an optional metal ligand.

The 1,4-dialkylcarboxylate-2,5-bis(N-arylamino)benzene compound is represented by Formula 1:

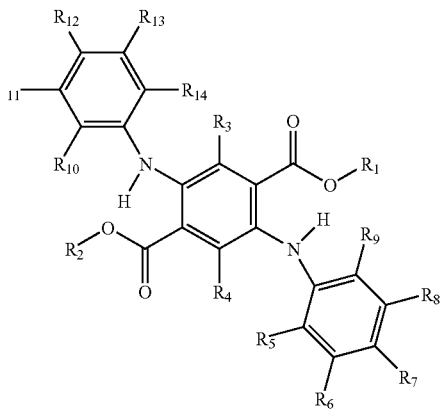

where $R_1$ and $R_2$ can be linear or branched hydrocarbons with less than 5 carbon atoms; $R_3$ and $R_4$ can be hydrogen, alkyl, aryl, alkoxy, fluorine, chlorine, bromine, nitro or cyano groups; $R_5$–$R_{14}$ may be for example hydrogen, halogen such as chlorine, bromine or fluorine, nitro, hydroxy, cyano, carboxyl, or groups which may be further substituted such as alkyl including branched or straight chain, such as methyl, trifluoromethyl, ethyl, alkoxy such as methoxy, ethoxy, propoxy, aryl such as phenyl, 2,4,6, trimethylphenyl, naphthyl, aryloxy such as phenoxy, tolyloxy, carbonamido such as acetamido, benzamido, acyl, such as acetyl, phenoxycarbonyl, sulfonyl such as methylsulfonyl, phenoxysulfonyl, acyloxy such as acetyloxy, benzoyloxy, N-substituted carbamoyl, N-substituted sulfamoyl, a heterocyclic oxy group or a heterocyclic thio group. When a molecule has two or more substituents, the substituents may join together to form a ring, such as a fused ring, unless otherwise provided. More preferably, the groups $R_1$ and $R_2$ may be ethyl or methyl, $R_3$ and $R_4$ may be hydrogen, fluorine, chlorine, bromine, methyl, ethyl, propyl, methoxy, ethoxy, phenyl, and $R_5$–$R_{14}$ may be the same as $R_3$ and $R_4$ plus nitro, trifluoromethyl, hydroxy, cyclohexyl, cyano. Most preferably, at least $R_5$ or $R_9$ and $R_{10}$ or $R_{14}$ are hydrogen. $R_6$ and $R_7$ or $R_8$ and $R_7$, or $R_{12}$ and $R_{13}$ or $R_{11}$ and $R_{12}$ can form a fused benzene ring, a cyclohexyl ring, or a oxazole ring.

The iodoaryl group is represented by Formula 2:

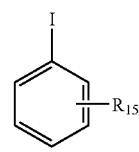

The particular substituents $R_{15}$ used, may be selected by those skilled in the art to attain the desired properties for a specific application and can include the same substituents broadly described above for $R_5$–$R_{14}$. More preferably, $R_{15}$ may be hydrogen, fluorine, chlorine, bromine, methyl, ethyl, propyl, methoxy, ethoxy, phenyl, nitro, trifluoromethyl, hydroxy, cyclohexyl, cyano. $R_{15}$ may be a fused ring with the parent benzene ring. Most preferably, $R_{15}$ may be hydrogen, methyl, ethyl, cyclohexyl, hydroxy, phenyl, methoxy, or ethoxy. Bulky substituents ortho to the iodine are not preferred and it is most preferred that at least one of the ortho position to the iodine be hydrogen.

The amount of the iodoaryl compound used, relative to the starting intermediate 1,4-dialkylcarboxylate-2,5-bis(N- arylamino) benzene as per formula 1, can range from 2–10 equivalents, more preferably higher than 2 equivalents. The base needed to perform the process may be a carbonate salt, a phosphate salt, NaOH, NaH, or an alkoxide. Most preferably the base used may be $K_2CO_3$, $Cs_2CO_3$, in the amount of 2 equivalents per Formula 1 or more, most preferably 2–2.5 equivalents.

The metal used to effect the coupling may be copper metal, copper(I)iodide, or copper(I)chloride, copper(I) oxide, or combinations thereof, in the amounts of 10 mole % or higher (mole percentage relative to formula 1). If copper is used alone, it is useful to provide about 2 equivalents per formula 1. More preferably, a combination of copper and copper(I)iodide, or copper and copper(I)chloride are used. Here, it is advantageous to provide copper as 20 mole % or more mole percentage (relative to Formula 1) and provide copper(I)chloride or copper(I)iodide as 10 mole % or more mole percentage relative to Formula 1. In any of these embodiments, a metal ligand such as 1,10-phenanthroline, or 1,2-trans-cyclohexyldiamine may be used as a metal ligand to accelerate the reaction. Its use is particularly useful if only a copper salt is used.

Under the reaction conditions stated above, the temperature needed to effect the coupling should be higher than 80° C., more preferably higher than 100° C., most preferably around 150° C. The temperature requirements are dictated by the nature of the substituents described in Formulas 1 and 2.

One may optionally employ a solvent to lower viscosity of the mixture. The solvent may be one that evaporates off during the reaction, or it may remain. Toluene and dichlorobenzene are non-limiting examples of useful solvents. Methylene chloride is not a preferred solvent because of environmental problems.

Synthesis of N,N'-diphenylquinacridone

The scheme of the overall substituted quinacridone synthesis is exemplified in the following steps to prepare Compound (7), N,N'-diphenylquinacridone. This invention is directed toward Step 3, but it is useful to understand some of the other steps that can be used to synthesize the aryl-substituted quinacridone.

STEP 1

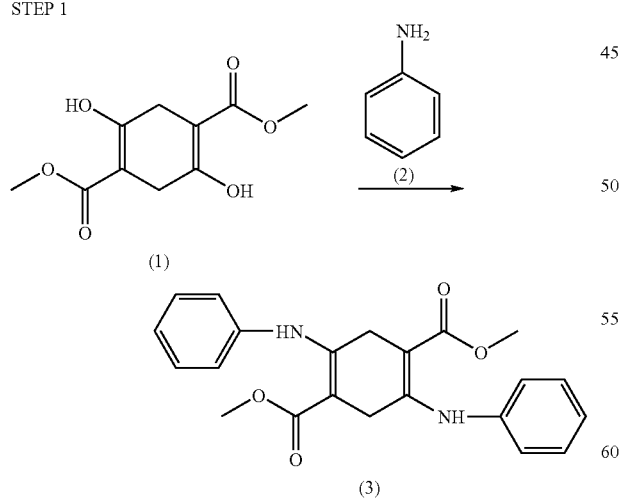

STEP 2

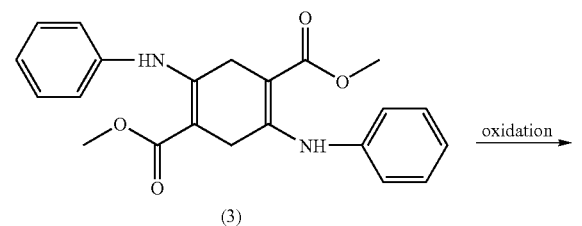

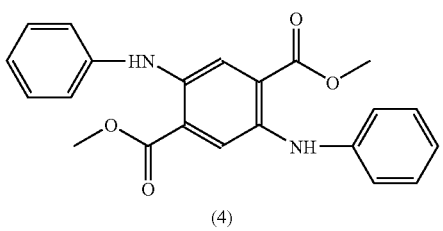

STEP 3

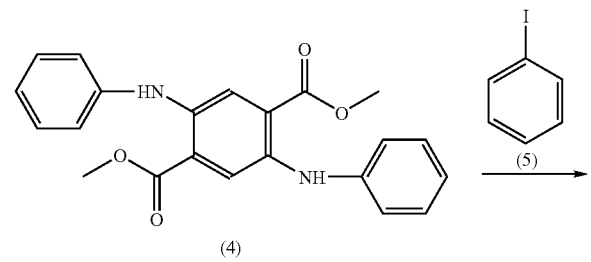

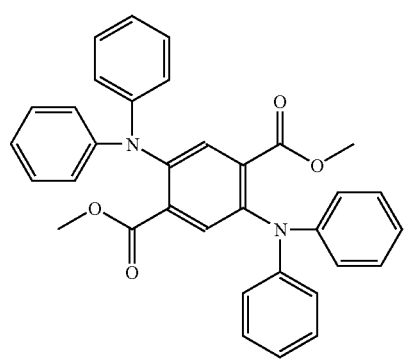

STEP 4

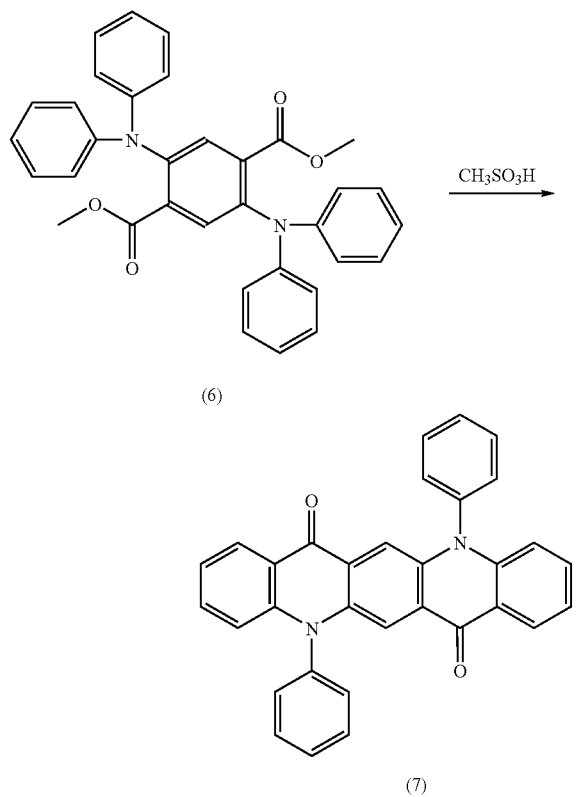

The process entails the condensation of the starting material (compound 1) with an aromatic amine compound (in this case aniline, compound 2) to form 1,4-cyclohexadiene-1,4-dimethylcarboxylate-2,5-bis(arylamine), compound 3. The next step is to oxidize the 1,4-cyclohexadiene compound (compound 3) to a benzene compound (compound 4), using a known method, preferably a mild method such as air oxidation. The resulting 1,4-dimethylcarboxylate-2,5-bis (arylamino) benzene is then reacted to replace the hydrogen on both arylamino groups with an additional aryl group, as by reaction with an iodoaryl reagent (in this case, iodobenzene, compound 5), as described previously in this invention. Next, the 1,4-dimethylcarboxylate-2,5-bis(N,N'-diaryl) compound (compound 6) can be hydrolyzed and condensed (cyclized) in one step by contacting the previous mentioned with methanesulfonic acid, to convert the compound into an N,N'-diphenylsubstituted quinacridone (compound 7). Depending on the nature of the aryl groups, this reaction can generate isomers.

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino,p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The Hammett's constant measures the relative electron withdrawing ability of a substituent on an aryl ring with more positive values being more electron withdrawing. Values are given in numerous handbooks such as Substituent Constants for Correlation Analysis in Chemistry and Biology, C. Hansch and A. J. Leo, Wiley, N.Y. (1979) and pKa Prediction for Organic Acids and Bases D. D. Perrin, B. Dempsey, and E. P. Serjeant, Chapman and Hall, New York (1981).

EXAMPLE

Preparation of 1,4-cyclohexadiene-1,4-dicarboxylic acid, 2,5 bis(phenylamino)-, Dimethyl Ester (3)

A 50 g (215 mmol, 1 eq) sample of 1,4-cyclohexanedione-2,5-dicarboxylate (1) was combined with a slight excess of aniline (2) (45 mL) in a 250 mL round bottom flask. The resulting neat mixture was brought to 80–90° C. for 4 h via heating mantle. Usually, the product precipitates out within the 4 hours of heating. The mixture is then removed from the heat, and while warm, methanol is added and the solid slurried in methanol. The product is isolated by filtration, washed with 100 mL methanol, then 50 mL of P950 ligroin, for drying, to yield 77 g (95%) of clean material. The product can be used for the next step, without further purification.

Preparation of 1,4-benzenedicarboxylic acid, 2,5-bis (phenylamino)-, Dimethyl Ester(4)

A 50 g sample of the compound (3) was partly dissolved in 1L of toluene, in a 2L, 3 neck round bottom flask. A reflux condenser was attached to one joint, one joint was plugged and the other was connected to a flow of air. The vigorously stirred mixture was brought just below reflux by means of a heating mantle, and a flow of air was generated at the surface of the liquid. After 4 h TLC showed no byproducts, and a 50% clean conversion of the cyclohexene intermediate to the aromatic product. The reaction was complete after 4 additional hours, with very little impurities present. The mixture was concentrated and the red solid residue was suspended in 50 mL of MeOH, the solid was isolated by filtration and washed with another portion of MeOH (50 mL), then P950 ligroin, to yield 90% (44.8 g) of a bright orange product. More of the product (4) can be recovered if the mother liquor is concentrated, chilled and the process above repeated.

Note: Alternatively, the oxidation can be carried out in methylene chloride, however the conversion does not take place as cleanly as in toluene, furthermore methylene chloride use in a production setting is not desirable for safety and disposal reasons.

Preparation of 1,4-benzenedicarboxylic acid, 2,5-bis (N,N'-diphenylamino),-dimethyl ester(6) (INVENTION)

A 40 g (97 mmol, 1 eq) sample of 1,4-benzenedicarboxylic acid, 2,5-bis(phenylamino)-, dimethyl ester (4), 65 mL (large excess necessary for ease of stirring) of iodobenzene (5), 27 g (194 mmol, 2 eq) of potassium carbonate, 12.3 g (197 mmol, 2 eq) of copper, and 3 g of copper(I)iodide were combined in a 250 mL round bottom flask. The resulting mixture was too thick to stir efficiently, so about 10 mL of toluene were also added for ease of stirring; the toluene gradually evaporated off. The mixture was refluxed overnight (around 150–160° C.). The originally red mixture turned greenish-brown. TLC indicated one spot with very little baseline impurities. The thick mixture was cooled to room temperature, slurried in methylene chloride (or THF) and the inorganic solids were removed by filtration. The solid residue which still contained product (6) was repeatedly washed with methylene chloride (or THF), and the washes were concentrated to a syrup. The concentrate was chilled in ice, the resulting solid was isolated by filtration, washed with MeOH, then with P950 ligroin. The bright yellow product was obtained in 85% yield (47 g). If so desired, the excess iodobenzene can be recovered and cleaned by distillation or filtration through a silica gel plug (eluting with P950 ligroin) and then reused.

Note: Alternatively, the reaction can be effected in the presence of catalytic amounts of Cu (20%) and CuI (10%). This is a more desirable process for a few reasons: ease of stirring of the reaction mixture; use of catalyst is minimized thus making the filtration of the inorganics more efficient and an environmentally more friendly process.

Preparation of Quino (2,3-b)acridine-7,14-dione, 5, 12-dihydro-5,12-diphenyl or N,N-diphenyl Quinacridone (7)

A 167 g (315 mmol) sample of compound (6) was suspended in about 200 mL of methanesulfonic acid. The thick suspension was quickly brought to 140° C. and the resulting blue mixture was stirred at the temperature for 4 h. The thick reaction mixture was cooled and slowly poured over ice (in a 1 L beaker), with vigorous stirring. The resulting reddish-brown suspension was left to stand such that the solid would settle and the aqueous phase could be decanted. The process was repeated twice, then one more time using $H_2O$ and $Na_2CO_3$ (aq, sat), in a 1:1 ratio. The solid was then isolated by filtration to yield 139 g (95%) of red-brown crude product. The crude material can be further purified with very little loss by slurring it in hot MeOH, stirring for 1 h, then cooling, and isolating it by filtration. The slurring process is then repeated using hot acetonitrile. The resulting solid is then washed with P950 ligroin (100 mL) for drying. The material so obtained can be further purified by sublimation.

The aryl-substituted quinacridone materials synthesized according to this invention may be incorporated in an emissive layer of an OLED device. To better control the characteristic behavior of such a device, it is desirable to choose the starting materials and reagents such that only one isomer is obtained, such as the case of compound (7). The nature of the aromatic amine in step 2, and the iodo-aryl reagent used in step 3 of the synthesis dictate the substitution pattern in the final N,N'-diarylsubstituted quinacridone.

The entire contents of the patents and other publications referred to in this specification are incorporated herein by reference.

What is claimed is:

1. A process comprising reacting a 1,4-dialkylcarboxylate-2,5-bis(N-arylamino) benzene with an iodoaryl compound in the presence of a base and copper in elemental form or in the (I) or (II) valence state to form the corresponding 2,5-bis(N-diarylamino) compound and then forming a quinacridone compound by subjecting the 2,5-bis(N-diarylamino) compound to a condensation reaction.

2. The process of claim 1 wherein the copper comprises Cu, CuI, $CuCl_2$, or $Cu_2O$.

3. The process of claim 1 wherein the iodoaryl compound is a substituted iodo-phenyl compound.

4. The process of claim 1 wherein the N-arylamino group is a N-phenylamino group.

5. The process of claim 1 wherein the dialkylcarboxylate is a dimethyl carboxylate.

6. The process of claim 1 wherein the benzene ring or at least one of the aryl groups is substituted with a group having a Hammett's σ constant at least 0.05 more positive than the corresponding methyl group.

7. The process of claim 6 wherein the substituted group is selected from the group consisting of halogen, aryl, an aromatic heterocycle, or a fused aromatic or heteroaromatic ring.

8. The process of claim 7 wherein the substituted group is selected from the group consisting of phenyl, biphenyl, and naphthyl groups.

9. The process of claim 1 wherein there are optionally up to 4 substituents on the aryl rings.

10. The process of claim 1 wherein the reaction is performed at a temperature of at least 80° C.

11. The process of claim 1 wherein the reaction is performed at a temperature of at least 100° C.

12. The process of claim 1 wherein the reaction is performed at a temperature of at least 150° C.

13. The process of claim 1 wherein the reaction is performed in the presence of an organic solvent having a boliling point of at least 80° C.

14. The process of claim 13 wherein the solvent comprises toluene or dichlorobenzene.

15. The process of claim 1 wherein the base is selected from carbonates, hydroxides, phosphates, alkoxy and hydrides.

16. A process for preparing an N, N'-diarylquinacidone capable of fluorescent emission in the green region comprising performing the reactions of claim 1 and then condensing the product to form a diarylquinacridone compound.

17. A process for forming an N, N'-diarylquinacridone compound comprising the steps of condensing a 1, 4-dialkylcarboxylate-2, 5-hydroxy 1, 4-cyclohexadiene with an arylamine to form the corresponding 1, 4-dialkylcarboxylate-2, 5-bis (arylamino) 1, 4-cyclohexadiene, followed by oxidation of the cyclohexadiene to the corresponding benzene compound, followed by the reactions of claim 1.

* * * * *